(12) United States Patent
Jones

(10) Patent No.: US 11,717,253 B2
(45) Date of Patent: Aug. 8, 2023

(54) SYSTEMS AND METHODS FOR RECORDING AND/OR MONITORING HEART ACTIVITY

(71) Applicant: Richard D. Jones, Katy, TX (US)

(72) Inventor: Richard D. Jones, Katy, TX (US)

( * ) Notice: Subject to any disclaimer, the term of this patent is extended or adjusted under 35 U.S.C. 154(b) by 434 days.

(21) Appl. No.: 16/692,179

(22) Filed: Nov. 22, 2019

(65) Prior Publication Data

US 2021/0153837 A1 May 27, 2021

(51) Int. Cl.
| | |
|---|---|
| *A61B 7/04* | (2006.01) |
| *A61B 5/021* | (2006.01) |
| *A61B 5/145* | (2006.01) |
| *A61B 7/02* | (2006.01) |
| *G16H 50/20* | (2018.01) |
| *G16H 10/60* | (2018.01) |

(52) U.S. Cl.
CPC ............ *A61B 7/04* (2013.01); *A61B 5/02141* (2013.01); *A61B 5/14542* (2013.01); *A61B 7/026* (2013.01); *A61B 2562/0204* (2013.01); *G16H 10/60* (2018.01); *G16H 50/20* (2018.01)

(58) Field of Classification Search
None
See application file for complete search history.

(56) References Cited

U.S. PATENT DOCUMENTS

| | | | | |
|---|---|---|---|---|
| 5,010,889 | A * | 4/1991 | Bredesen | A61B 7/04 600/528 |
| 6,498,854 | B1 | 12/2002 | Smith | |
| 7,035,684 | B2 * | 4/2006 | Lee | A61N 1/05 600/513 |
| 7,517,328 | B2 * | 4/2009 | Hoffmann | A61H 31/00 601/48 |
| 8,079,968 | B2 * | 12/2011 | Hoffmann | A61B 17/225 601/48 |
| 8,764,674 | B2 * | 7/2014 | Song | A61B 7/00 600/528 |
| 8,870,796 | B2 * | 10/2014 | Hoffmann | A61B 8/483 601/48 |
| 9,345,432 | B2 * | 5/2016 | Salisbury | A61B 7/003 |
| 9,545,228 | B2 * | 1/2017 | Bardy | A61B 5/259 |
| 9,610,059 | B2 * | 4/2017 | Christensen | A61B 5/02028 |

(Continued)

OTHER PUBLICATIONS

American Diagnostic Corporation, The Adscope® 658 Electronic Scope, "Hearing Is Believing", 2017.

(Continued)

*Primary Examiner* — Shirley X Jian
(74) *Attorney, Agent, or Firm* — Winstead PC

(57) ABSTRACT

A system for monitoring heart activity may provide a power source, digital storage, a processor, a main body with an alignment mechanism facilitating proper placement, and one or more microphones for receiving audio signals and positioned for placement at auscultatory areas. The alignment mechanism may be a dip, depression, notch, or combinations thereof that align the system centrally on the sternum, suprasternal notch, or jugular notch. Further, the audio signals from the microphones may be monitored or recorded as individual tracks corresponding to different auscultatory areas. The auscultatory areas may be selected from an aortic area, pulmonic area, tricuspid area, mitral area, Erb's point, first alternate tricuspid area, and/or second alternate tricuspid area.

19 Claims, 3 Drawing Sheets

(56) References Cited

U.S. PATENT DOCUMENTS

| | | | |
|---|---|---|---|
| 9,955,939 B2* | 5/2018 | Sezan | A61B 7/00 |
| 10,130,267 B2* | 11/2018 | Song | A61B 7/003 |
| 10,925,573 B2* | 2/2021 | Martin | B06B 1/085 |
| 11,045,144 B2* | 6/2021 | Zhou | A61B 5/7257 |
| 11,045,163 B2* | 6/2021 | Laska | G10L 25/06 |
| 2002/0082508 A1* | 6/2002 | Ogura | A61B 7/04 |
| | | | 600/490 |
| 2004/0167416 A1* | 8/2004 | Lee | A61N 1/05 |
| | | | 600/513 |
| 2005/0054958 A1* | 3/2005 | Hoffmann | A61B 17/225 |
| | | | 977/905 |
| 2008/0082004 A1* | 4/2008 | Banet | A61B 5/6833 |
| | | | 600/485 |
| 2008/0114266 A1* | 5/2008 | Shen | A61B 7/04 |
| | | | 600/586 |
| 2008/0146276 A1* | 6/2008 | Lee | A61B 5/6887 |
| | | | 455/556.1 |
| 2008/0228095 A1* | 9/2008 | Richardson | A61B 7/026 |
| | | | 600/528 |
| 2009/0012433 A1* | 1/2009 | Fernstrom | A61B 5/0022 |
| | | | 600/593 |
| 2009/0099479 A1* | 4/2009 | Solanki | A61M 16/0488 |
| | | | 128/207.14 |
| 2011/0288421 A1* | 11/2011 | Banet | A61B 5/021 |
| | | | 600/485 |
| 2012/0029308 A1* | 2/2012 | Paquet | A61B 5/01 |
| | | | 600/549 |
| 2012/0271199 A1* | 10/2012 | Salisbury | A61B 5/4818 |
| | | | 600/586 |
| 2013/0109989 A1* | 5/2013 | Busse | A61B 5/029 |
| | | | 600/527 |
| 2013/0237862 A1* | 9/2013 | Song | A61N 1/36585 |
| | | | 600/490 |
| 2013/0237863 A1* | 9/2013 | Song | A61M 5/1723 |
| | | | 607/18 |
| 2015/0190109 A1* | 7/2015 | Christensen | A61B 5/0004 |
| | | | 600/528 |
| 2015/0190110 A1* | 7/2015 | Chong | A61B 7/003 |
| | | | 600/528 |
| 2016/0296166 A1* | 10/2016 | Bardy | A61B 5/6832 |
| 2017/0079612 A1* | 3/2017 | Park | H04R 1/46 |
| 2017/0215835 A1* | 8/2017 | Sezan | A61B 7/026 |
| 2018/0116626 A1* | 5/2018 | Darbari | A61B 5/6898 |
| 2019/0069088 A1* | 2/2019 | Seiler | H04R 1/025 |
| 2019/0083038 A1* | 3/2019 | Griffin | G06F 16/686 |
| 2019/0099152 A1* | 4/2019 | Martin | B06B 1/0688 |
| 2021/0059586 A1* | 3/2021 | Marriott | A61B 5/7203 |
| 2021/0145306 A1* | 5/2021 | Karankevich | A61B 5/7267 |

OTHER PUBLICATIONS

Eko Devices Inc., Core Digital Stethoscope, https://shop.ekohealth.com/products/core-digital-stethoscope, Feb. 20, 2020.

3M Health Care, 3M Littmann Electronic Stethoscopes, "Redefining what a stethoscope can do for you", www.Littmann.com, 2012-2013.

Thinklabs, Thinklabs One Digital Stethoscope, https://www.thinklabs.com/one-digital-stethoscope, Feb. 20, 2020.

* cited by examiner

SYSTEMS AND METHODS FOR RECORDING AND/OR MONITORING HEART ACTIVITY

FIELD OF THE INVENTION

This invention relates to systems and methods recording and/or monitoring heart activity. More particularly, to recording or monitoring heart sounds.

BACKGROUND OF INVENTION

Tens of millions in the United States have undetected heart disease. CHDs (Congenital Heart Defects) are the most common birth defects. One in seventy-seven U.S. children had a current heart condition in 2016. 610,000 people die of heart disease in the USA annually. Various devices exist for monitoring blood pressure, oxygen level, electrocardiogram, or the like, but such devices do not measure enough to detect a wide variety of heart issues.

While heart conditions can be detected with a stethoscope, there are several problems with such techniques. A skilled doctor with a good ear is needed to detect most issues. Doctors require training for determining correct placement of the stethoscope, as well as training to identify sounds that are problematic. Non-doctors do not typically have the necessary training. Further, doctors must also maintain a trained ear with good sensitivity, which may unfortunately deteriorate with age.

Systems and methods discussed further herein record and/or monitor heart activity, including recording or monitoring heart sounds, remedying many of the drawbacks of other devices.

SUMMARY OF INVENTION

In one embodiment, a system for monitoring heart activity comprises a power source, digital storage, a processor, a main body with an alignment mechanism facilitating proper placement, and one or more microphones for receiving audio signals and positioned for placement at auscultatory areas. The alignment mechanism may be a dip, depression, notch, or combinations thereof that align the system centrally on the sternum, suprasternal notch, or jugular notch. Further, the audio signals from the microphones may be monitored or recorded as individual tracks corresponding to different auscultatory areas. The auscultatory areas may be selected from an aortic area, pulmonic area, tricuspid area, mitral area, Erb's point, first alternate tricuspid area, and/or second alternate tricuspid area.

In another embodiment, a method for monitoring heart activity is provided. The method comprising placing the alignment mechanism of a heart monitoring system at a desired location, wherein the placement results in alignment of one or more microphones of the heart monitoring system at auscultatory areas suitable for monitoring heart sounds. Recording or monitoring of audio signals may be initiated with the one or more microphones, wherein the audio signals from each of the one or more microphones are individual tracks. The audio signals may be analyzed to evaluate whether a heart condition is present and results may be displayed. The auscultatory areas may be selected from an aortic area, pulmonic area, tricuspid area, mitral area, Erb's point, first alternate tricuspid area, and/or second alternate tricuspid area.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1:
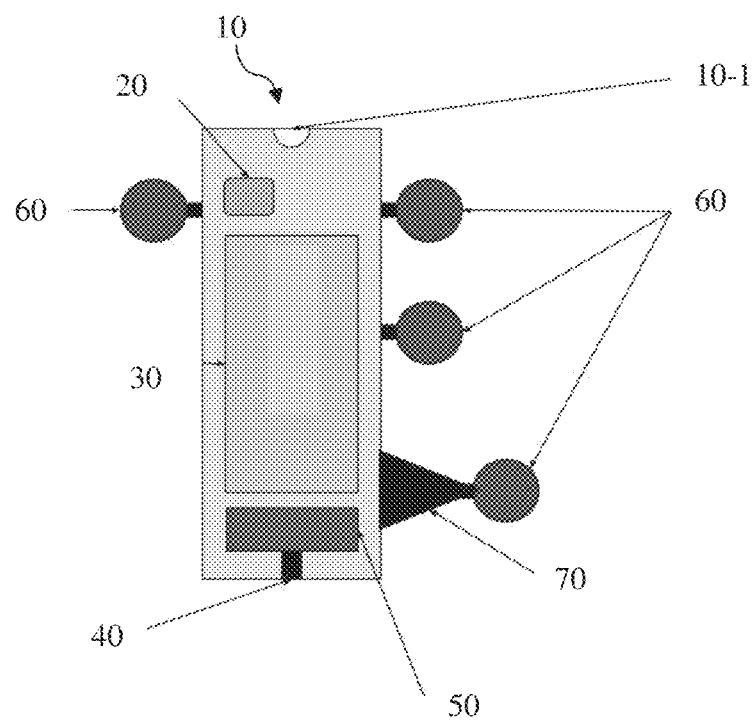
FIG. 1 is an illustrative embodiment of a heart activity monitoring system.

Refer now to the drawings wherein depicted elements are not necessarily shown to scale and wherein like or similar elements are designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The terms "monitor" or "detect" as utilized herein shall be understood to mean the systems and/or methods may monitor, detect, observe, or sense signals, as well as record such signals. The term "record" or "store" as utilized herein shall be understood to include direct recording to a system or transfer and recording to a remote location.

Systems and methods discussed further herein record and/or monitor heart activity to detect heart issues. In some embodiments, the systems and methods record or monitor heart sounds, such as with one or more stethoscope microphones. The systems and methods allow for placement and operation by an untrained individual, and do not require operation by a trained physician. In some embodiments, multiple tracks may be recorded or monitored from multiple, distinct auscultation points. The systems and methods may also analyze data to determine if potential heart issues are present. In some embodiments, recordings may be compared to prior recordings of the same person. In some embodiments, recordings may be compared to recordings of known diagnosed problems.

FIG. 1 is an illustrative embodiment of an improved heart activity monitoring system. A main body 10 provides the main structure of the system. Embodiments of the main body may include different sizes (e.g. infant, child, adult, and tall). However, other embodiments may provide an adjustable main body that allows adjustment of the length and/or microphone 60 positions. Main body 10 provides an alignment mechanism 10-1, such as notch, depression, and/or the like, facilitation proper placement of the system. As a nonlimiting example, the alignment mechanism 10-1 may be shaped, such as with a dip, depression, notch or combinations thereof, in a manner that aligns the system centrally on the sternum, such as the suprasternal or jugular notch. In some embodiments, the main body 10 may optionally include additional components or in place of the notch/depression as part of the alignment mechanism. For example, in some embodiments, optional accelerometer(s) or other sensor(s) may be provided to detect if the main body 10 has been correctly placed vertically on the wearer. For example, in some embodiments, an optional microphone may be provided by for placement at the sternum, suprasternal notch, or jugular notch, thereby allowing monitoring/recording of flow through the aorta. It shall be apparent that the detection of the presence or absence of aortic sounds may be used to detect correct placement. Main body 10 may be generally shaped in any suitable manner as long as the alignment mechanism 10-1 is not impeded. As a nonlimiting example, the main body 10 may be a general rectangular shape and approximately the length of the sternum. Further, some embodiments may optionally provide a back surface contoured to fit closely against a user's body. In some embodiments, the system may further comprise a securing means, such as a Velcro strap or the like, that allows the system to be secured in a desired position. It shall be apparent to one of ordinary skill that the system is particular suitable to humans. However, other embodiments may be suitable for various animals and may require minimal modification. In some embodiments, the main body 10 may provide optional interface components, such as operation buttons 20, a display 30, connectors 40, indicators, or the like. In some embodiments, operation button(s) 20 may include buttons to initiate and stop recording/monitoring. In some embodiments, display 30 may be any suitable display, such as a LCD or the like, and may display detected audio signals, results, menus, or the like. Optionally, display 30 may be a touchscreen display allowing system operation controls to be controlled via the touchscreen. In some embodiments, connectors 40 may be a USB, 1394, firewire, audio jack, or any other known connector. In some embodiments, indicators, including both audio and visual, may be provided, such as when a display is absent, that indicate operation mode, such as whether the system is on/off, recording/monitoring, properly placed, or the like.

Additionally, embodiments of the system may further comprise various electronic components 50 to support features provided. In some embodiments, a power source providing power for the system; digital storage storing gathered data and/or software/firmware for various operations; processor, microprocessor, or CPU for controlling various operations; digital recorder recording audio data; encoder/decoder for the data; and mixer/sampler for processing data if desired. In some embodiments, may include further optional electronic components or hardware. Nonlimiting examples may include Bluetooth, Wi-Fi, or the like. In some embodiments, the system may optionally communicate data, such as via USB, firewire, Bluetooth, Wi-Fi, or the like, with external devices, such as a cellphone, laptop, desktop, handheld electronic device, cloud storage/computing, or the like. In embodiments involving optional external devices, the system's operation controls may be optionally controlled remotely via the external device. As a nonlimiting example, an application may be provided on a cellphone that allows remote control of the system, such as powering on the system, initiating monitoring/recording, initiating display of results, etc.

Embodiments of the system further comprise one or more microphones 60 for receiving audio signals. Further embodiments discussing implementations involving one or more microphones are discussed in more detail below. As shown, microphones 60 may be optionally coupled to the main body 10 via any suitable bracket mechanism 70. Microphones 60 may be any suitable microphone, such as an electronic stethoscope. In some embodiments, main body 10 may allow microphone(s) 60 and/or bracket mechanism(s) to be added or removed as desired. In some embodiments, an amplifier may optionally be provided to amplify detected sounds, including traditional or software based amplifier(s). In some embodiments, a soundproof skirt (not shown) may be provided to minimize or dampen ambient noise. As a nonlimiting example, microphones 60 may be covered by a soundproof skirt, such a thin, neoprene cover. In some embodiments, a desired placement location may facilitate attachment to the main body 10 without a bracket mechanism 70 depending on the size and shape of the main body. In a preferred embodiment, the bracket mechanism 70 is sufficiently rigid to facilitate correct alignment and placement of microphone(s) 60, which allows relevant heart signals (discussed in detail below) to be gathered. Other embodiments may involve flexible, semi-rigid, or adjustable bracket mechanisms 70, but may also include components to facilitate detection to identify proper placement. In some embodiments, the system may optionally include further sensors or the like, which may optionally be incorporated with the microphone assembly, for detecting desired parameters. In some embodiments, electrodes may optionally be provided to provide ECG/EKG data. In some embodiments, an oxygen saturation sensor may optionally be provided to provide blood oxygen saturation readings (e.g. $SpO_2$). In some embodiments, a blood pressure sensor may optionally be provided to provide blood pressure readings.

Figure 2:
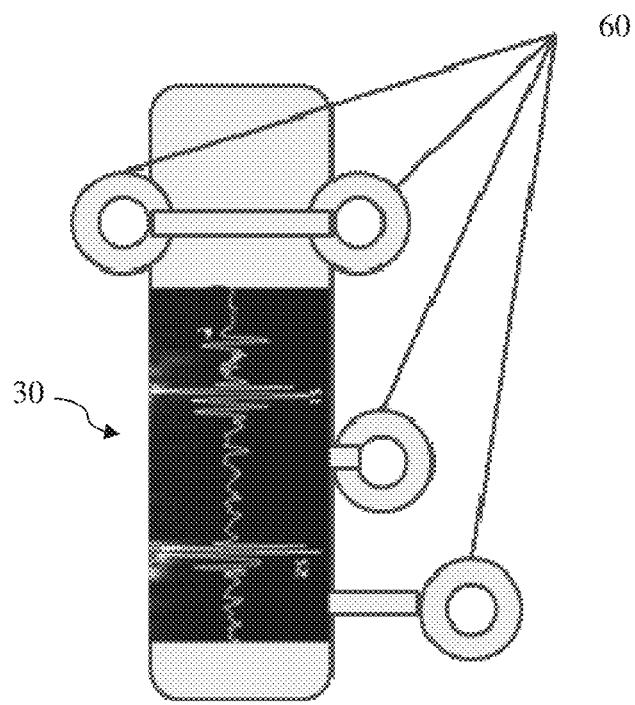
FIG. 2 shows a nonlimiting example of a heart activity monitoring system.

FIG. 2 shows a nonlimiting example of a heart activity monitoring system. As shown, microphones receive audio and may optionally display the audio signals received. Each microphone monitors audio signals from different locations, and the recorded audio signals from each location can be considered to be a track or channel. In some embodiments, the audio tracks or channels corresponding to different microphones are recorded as individual tracks or channels. In some embodiments, the display may be toggled to show the track or audio of different microphones or multiple tracks. Additionally, the display may further display EKG/ECG, oxygen saturation, blood pressure, heart rate, or other readings.

Figure 3:
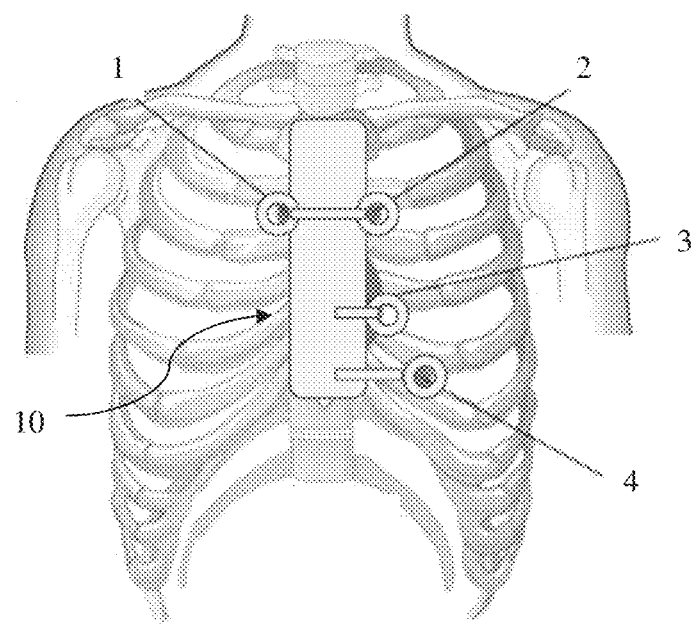
FIG. 3 shows a nonlimiting example of placement of a system on a user.

In some embodiments, the one or more microphones are positioned to detect desired audio from desired circulatory areas, such as desired auscultatory areas. Nonlimiting examples include aortic, pulmonic, tricuspid, mitral, Erb's point, or the like. In one embodiment, four microphones may be desired for placement at desired auscultatory areas. FIG. 3 shows a nonlimiting example of placement of a system on a user. As shown, the main body facilitates placement of the top of system near the suprasternal or jugular notch, and may extend towards the epigastric region. In the nonlimiting example shown, four microphones are positioned near the right second interspace aortic area 1, left second interspace pulmonic area 2, tricuspid or left sternal boarder or right ventricular area 3, and apex left ventricular or mitral area 4.

Figure 4:
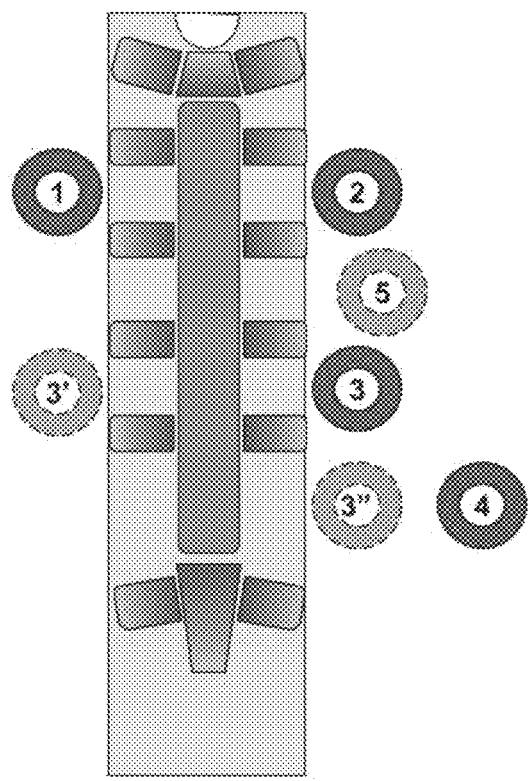
FIG. 4 shows potential embodiments of desired placement of microphones on a user.

FIG. 4 shows potential embodiments of desired placement of microphones on a user. Solid lines indicate preferred locations, whereas broken lines illustrate locations that may also be of interest. Depending on the number of microphones present in the system, it may be desirable to place one or more of the microphones in an aortic area 1 (S2), pulmonic area 2 (S2), tricuspid area 3 (S1), mitral area 4 (S1), Erb's point 5 (S1,S2), first alternate tricuspid area 3' (S1), and/or second alternate tricuspid area 3" (S1). In one preferred embodiments, the system may comprise four microphones with one placed in the aortic area, one in the pulmonic area, one in the tricuspid area, and one in the mitral area. Other embodiments may include more or fewer microphones, each placed in one of the seven areas illustrated. The audio signal(s) or track(s) collected for different auscultatory areas may be analyzed to evaluate whether any heart conditions of concern are present. As a nonlimiting example, the processor of the system or cloud computing may be utilized to analyze the tracks, as discussed further in the methods detailed below. In some embodiments, the audio signals may be compared to a database of audio signals indicative of heart conditions or heart condition data. As a nonlimiting example, the database may provide sample audio signals arranged by heart conditions, such as audio files representative of arrhythmia, representative of heart valve issues, etc. In some embodiments, the heart condition data may include prior, historic data of the individual utilizing the system and/or data from multiple individuals. In some embodiments, heart condition data may be generated based on artificial intelligence, machine learning, deep learning, combinations thereof, or the like, as discussed further in the methods detailed below.

Figure 5:
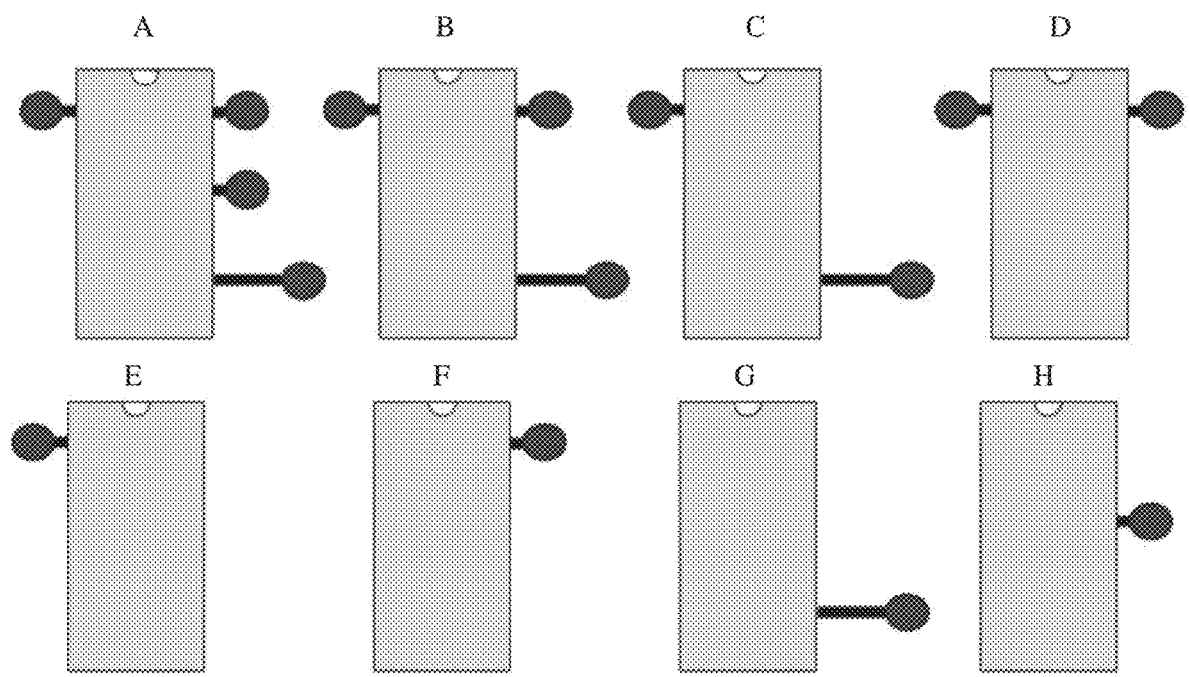
FIG. 5 illustrates nonlimiting examples of different permutations for placement of one or more microphones.
Figure 6:
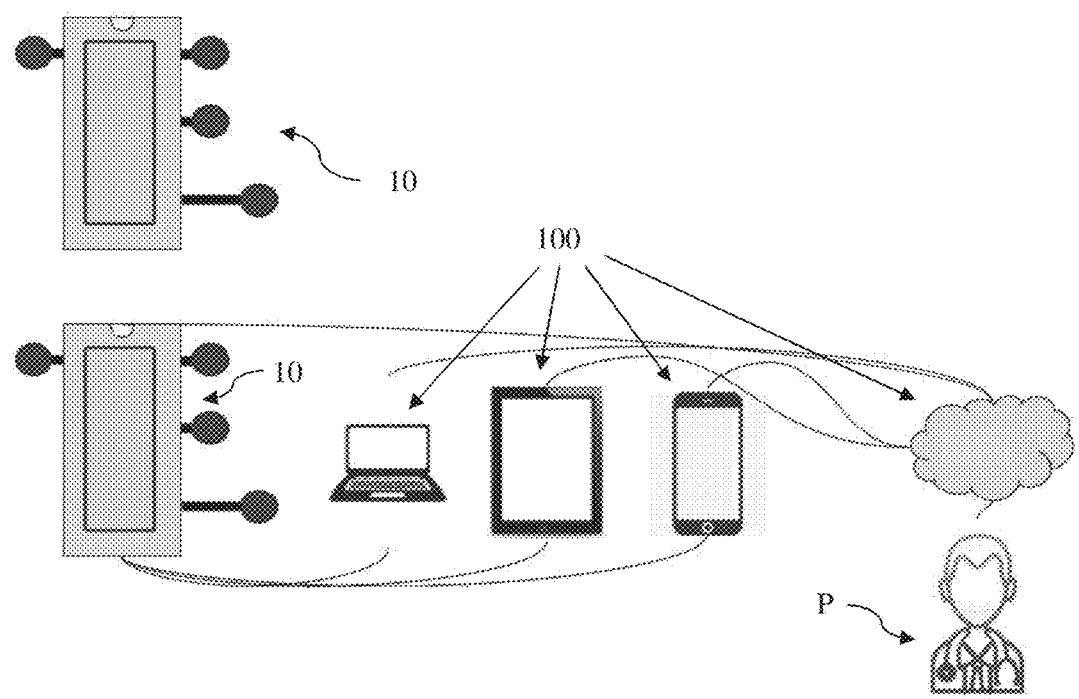
FIG. 6 illustrates embodiments of modes of operation for a system.

FIG. 5 illustrates nonlimiting examples of different permutations for placement of one or more microphones for the system. From top left to bottom right:

(A) aortic, pulmonic, tricuspid, and mitral
(B) aortic, pulmonic, and mitral
(C) aortic and mitral
(D) aortic and pulmonic
(E) aortic
(F) pulmonic
(G) mitral
(H) tricuspid FIG. 6 illustrates embodiments of modes of operation for the system 10. It shall be understood that one or more of the operation modes may be provided in different embodiments. In a standalone mode, the system 10 may record heart sounds and diagnose potential issues via means discussed previously. As a nonlimiting example, sounds may be monitored via microphones and recorded; and firmware/software may allow diagnosis of heart conditions based on detected audio data. Further, results may be displayed to the user. In an embodiment of a remote mode, the system 10 may be connected to a remote device or cloud computing 100, such as a cellphone, handheld device, laptop or PC, etc., via a wired or wireless connection (e.g. USB, firewire, Bluetooth, Wi-Fi, or any other suitable connection). As a nonlimiting example, it may be desirable to minimize the system. As such, it may be desirable to minimize processing power and provide diagnostics remotely via the remote device or cloud computing 100. The remote device or cloud computing 10 may receive the detected audio data via the wired or wireless connection to allow analysis of the data to be performed remotely. In some embodiments, the remote device or cloud computing may provide access to another individual P different from the user, such as the user's authorized physician or the like. In some embodiments, the remote mode may optionally allow for access to a database, such as an internet accessible database or cloud database, which contains data for diagnosis. For example, the diagnosis data may provide data files indicative of heart conditions, such as aortic regurgitation, aortic stenosis, hypertrophic cardiomyopathy, mitral regurgitation, mitral stenosis, myocarditis, pulmonary valve stenosis, arrhythmogenic RV dysplasia, commotio cordis, or the like, which would allow comparison to recorded audio data to determine if a heart condition is present. In further embodiments, the system may optionally include further sensors, when necessary, and allow further detection of additional heart conditions, such as arrhythmia, heart disease, heart defects, coronary artery diseases (CAD) such as angina and myocardial infarction (commonly known as a heart attack). Other CVDs include stroke, heart failure, hypertensive heart disease, rheumatic heart disease, cardiomyopathy, abnormal heart rhythms, congenital heart disease, valvular heart disease, carditis, aortic aneurysms, peripheral artery disease, thromboembolic disease, and venous thrombosis, or the like.

Methods for monitoring heart activity are discussed herein, particularly for the systems discussed above, but not limited to such systems. In some embodiments, an alignment mechanism, such as notch, depression, and/or the like, is present to facilitate proper placement of the system at a desired location of a human or other animal. As a nonlimiting example, the alignment mechanism may be dip, depression, notch or combinations thereof of a heart activity monitoring system that aligns the system centrally on the sternum, such as the suprasternal or jugular notch. This step of placing the alignment mechanism at a desired location results in alignment of one or more microphones at positions suitable for monitoring heart sounds (e.g. FIG. 3). In other embodiments where microphones are adjustable, each microphone and/or bracket may be optionally adjusted to position the microphones desired locations. Further, some embodiments may provide an optional check step performed to determine if microphones are placed correctly, such as by monitoring audio to determine if audio corresponds to correct locations. As nonlimiting examples, some embodiments may compare detected aortic signals with the mitral signals, and/or the S1, S2 signals should match when properly amplified. In yet another nonlimiting example, an amplified aortic S1 signal should match similarly amplified S2 signal of the mitral area, or the device is misplaced. S1 and S2 will not match, but the amplification required will be consistent if placement is proper. When an optional securing means is present, the system may then be secured to the wearer if necessary. Next, the system may be powered on—however, it shall be recognized this power on step may occur at any time in the sequence before electronic features are used, such as before the optional microphone location check step discussed previously. In embodiments involving optional external devices, the system's operation controls may be optionally powered on remotely via an external device.

In some embodiments, monitoring and/or recording of signals detected by the microphones may be initiated when desired, such as by operational controls or may automatically begin when the system is powered on. Real-time display of the audio signal(s) detected may optionally be provided to a system display, or to an external device if present. An operator may optionally toggle between different views, such as a view showing multiple audio signals, operator selected audio signals, or an individual audio signal corresponding to a desired location to be viewed. Further, the operator may also re-play audio signals if desired. The audio signals from each of the one or more microphones may be recorded as individual tracks or channels. Concurrent with or after recording, the audio signal(s) may be analyzed to evaluate whether any heart conditions of concern are present. In some embodiments, the audio signals may be compared to a database of audio signals indicative of heart conditions or heart condition data. As a nonlimiting example, the database may provide sample audio signals arranged by heart conditions, such as audio files representative of arrhythmia, representative of heart valve issues, etc. In some embodiments, the heart condition data may include prior, historic data of the individual utilizing the system and/or data from multiple individuals. This heart condition data may be provided locally, remotely, via the cloud, or the like. In some embodiments, the heart conditions data may include data indicative of the auscultatory area of interest, thereby indicating which track it should be compared to. In some embodiments, the heart condition data may include indicators that provide an indication of metric(s) to be searched for in the audio signal.

In yet another embodiment, the heart condition data may be generated based on artificial intelligence, machine learning, deep learning, combinations thereof, or the like. In some embodiments, a central database or cloud database may be provided with heart condition data, which may be audio database data indicative of various different heart conditions in some cases or other data reliant on sensors other than microphones, e.g. aortic regurgitation, aortic stenosis, hypertrophic cardiomyopathy, mitral regurgitation, mitral stenosis, myocarditis, pulmonary valve stenosis, arrhythmogenic RV dysplasia, commotio cordis, arrhythmia, heart disease, heart defects, coronary artery diseases (CAD), angina, myocardial infarction, stroke, heart failure, hypertensive heart disease, rheumatic heart disease, cardiomyopathy, abnormal heart rhythms, congenital heart disease, valvular heart disease, carditis, aortic aneurysms, peripheral artery disease, thromboembolic disease, venous thrombosis, etc. The audio database data may include information on auscultatory areas of interest to detect such condition, one more tracks of audio signal data corresponding to such auscultatory areas, and/or metrics to be searched for in comparative audio signals. The central database and cloud database may have a sizeable collection of audio database data for each heart condition of interest. As a nonlimiting example, regular analysis of the database may be conducted via artificial intelligence, machine learning, deep learning, combinations thereof, or the like to update detection of heart conditions of interest. In some embodiments, individual heart monitoring systems may contribute data (e.g. anonymously) to the database, thereby regularly growing the database. In some embodiments, the database may provide updates to individual heart monitoring systems and/or remote external devices if necessary, such as updates to auscultatory areas of interest, indicators of interest, or the like for a heart condition.

In some embodiments, it may be optionally desirable to share recorded audio tracks with another individual, such as physician. As such, an optional share function (e.g. automatic or operator initiated) may be provided that allows the recorded audio tracks to be shared with another individual.

Once the audio signal(s) or tracks have been analyzed, the results may be displayed. In some embodiments, it may be optionally desirable to share results with another individual, which may be offered in the same manner as audio tracks. As a nonlimiting example, the results may provide an indication that no potential heart conditions were found; that minor conditions were found, optionally with an indication of the condition of concern (e.g. indications blood pressure levels of low risk), or that serious conditions of concern were found, optionally with an indication of the condition found. In some embodiments, the results may be optionally shared with an individual, such as when minor or serious conditions are found, with indicators of the severity of the condition and condition found. As a nonlimiting example, detection of a severe condition may trigger sharing the results with a preferred physician, ER, or the like.

Embodiments described herein are included to demonstrate particular aspects of the present disclosure. It should be appreciated by those of skill in the art that the embodiments described herein merely represent exemplary embodiments of the disclosure. Those of ordinary skill in the art should, in light of the present disclosure, appreciate that many changes can be made in the specific embodiments described, including various combinations of the different elements, components, steps, features, or the like of the embodiments described, and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure.

What is claimed is:

1. A strapless system for monitoring heart activity, the system comprising:
   a power source providing power;
   digital storage for storing data;
   a processor communicatively coupled to the digital storage and configured for controlling operation of the system;
   a main body configured to house the power source, digital storage, and the processor, wherein the main body includes an alignment mechanism comprising a dip, depression, notch or combinations thereof that is located on a top edge of the main body and configured to align with a suprasternal or jugular notch of an observed person for facilitating proper placement of the system on the observed person; and
   a plurality of microphones for receiving audio signals, wherein the plurality of microphones are coupled to the main body, and the plurality of microphones are positioned for placement at auscultatory areas.

2. The system of claim 1, wherein the audio signals from each of the plurality of microphones are individual tracks, and the auscultatory areas are selected from an aortic area, pulmonic area, tricuspid area, mitral area, Erb's point, first alternate tricuspid area, or second alternate tricuspid area.

3. The system of claim 1, wherein the processor is configured to analyze the audio signals to evaluate whether heart conditions are present by comparing the audio signals to heart condition data.

4. The system of claim 3, wherein the heart condition data is data generated based on artificial intelligence, machine learning, deep learning, or combinations thereof.

5. The system of claim 3, wherein the processor is configured to compare the audio signals to a database providing sample audio signals arranged by heart conditions, and wherein the heart condition data includes prior, historic data of multiple individuals.

6. The system of claim 3, wherein the heart condition data includes prior, historic data of the individual utilizing the system.

7. The system of claim 1 further comprising one or more bracket mechanisms, wherein the one or more bracket mechanisms comprise a proximal end attached to the main body and a distal end to which the one or more microphones are coupled.

8. The system of claim 1 further comprising a display, wherein the display is capable of showing the audio signals received by the plurality of microphones.

9. The system of claim 1, wherein each microphone of the plurality of microphones comprises a soundproof skirt.

10. The system of claim 1, wherein the main body comprises a back surface that is contoured to fit against the observed person's body.

11. The system of claim 1, further comprising an accelerometer configured to detect whether the main body is correctly placed vertically.

12. A method for monitoring heart activity with a heart monitoring system, the heart monitoring system comprising a main body that houses a processor and digital storage, the method comprising the steps of:
   aligning the main body so that a dip, depression, notch or combinations thereof that is located on a top edge of the main body aligns with a suprasternal or jugular notch of an observed person, wherein the aligning results in alignment of a plurality of microphones of the heart monitoring system at auscultatory areas suitable for monitoring heart sounds;
   initiating, via the processor, recording or monitoring of audio signals with the plurality of microphones, wherein the audio signals from each of the plurality of microphones are individual tracks;
   analyzing, via a remote device, the audio signals to evaluate whether a heart condition is present; and
   displaying, via the processor, results of the analysis of the audio signals.

13. The method of claim 12, wherein the analyzing step is performed by comparing the audio signals to heart condition data.

14. The method of claim 13, wherein the heart condition data is generated based on artificial intelligence, machine learning, deep learning, or combinations thereof.

15. The method of claim 13, wherein the audio signals are compared to a database providing sample audio signals arranged by heart conditions.

16. The method of claim 13, wherein the heart condition data includes prior, historic data of multiple individuals.

17. The method of claim 12, wherein the heart monitoring system comprises a back surface that is contoured to fit against the observed person's body.

18. The method of claim 12, further comprising monitoring, via the processor, an accelerometer associated with the heart monitoring system to determine whether the heart monitoring system is correctly placed vertically.

19. A method for monitoring heart activity with a heart monitoring system, the heart monitoring system comprising a main body that houses a processor and digital storage, the method comprising the steps of:
   aligning the main body so that a dip, depression, notch or combinations thereof that is located on a top edge of the main body aligns with a suprasternal or jugular notch of an observed person, wherein the aligning results in alignment of a plurality of microphones of the heart monitoring system at auscultatory areas suitable for monitoring heart sounds;
   initiating, via the processor, monitoring of audio signals of the plurality of microphones, wherein the audio signals from each of the one or more microphones are individual tracks;
   comparing, via the processor, the monitored audio signals, wherein the comparing comprises comparing detected aortic signals with mitral signals to determine if the signals match when amplified;
   analyzing, via a remote device, the audio signals to evaluate whether a heart condition is present; and
   displaying, via the processor, results of the analysis of the audio signals.

* * * * *